United States Patent [19]
Copley et al.

[11] Patent Number: 5,614,376
[45] Date of Patent: Mar. 25, 1997

[54] METHOD FOR FACILITATING TISSUE SLIDE PREPARATION

[75] Inventors: Dianne M. Copley, Arvada; Cindy K. Gallegos, Aurora, both of Colo.

[73] Assignee: Dicin Resources, Inc., Arvada, Colo.

[21] Appl. No.: 646,962

[22] Filed: May 8, 1996

Related U.S. Application Data

[63] Continuation of Ser. No. 326,324, Oct. 20, 1994, abandoned.
[51] Int. Cl.$^6$ .................... C12Q 1/00; G01N 1/00
[52] U.S. Cl. .................. 435/30; 435/1.1; 435/40.52; 436/63
[58] Field of Search ............... 435/30, 31, 292, 435/287, 294, 295; 401/40, 41, 42, 43, 136, 137, 138, 196, 198, 199; 422/58, 56, 61, 50; 436/63; 604/3

[56] References Cited

U.S. PATENT DOCUMENTS

| | | | |
|---|---|---|---|
| 1,287,487 | 12/1918 | Smith | 401/196 |
| 2,371,667 | 3/1945 | Arena et al. | 401/132 |
| 3,386,793 | 6/1968 | Stanton | 401/132 |
| 3,403,961 | 10/1968 | Gazzani | 401/202 |
| 3,466,131 | 9/1969 | Arcudi | 401/132 |
| 3,636,922 | 1/1972 | Ketner | 118/264 |
| 3,768,916 | 10/1973 | Avery | 401/132 |
| 3,891,331 | 6/1975 | Avery | 401/132 |
| 4,183,684 | 1/1980 | Avery, Jr. | 401/133 |
| 4,740,194 | 4/1988 | Barbabino et al. | 604/3 |
| 5,192,688 | 3/1993 | Switzer et al. | 436/63 |

*Primary Examiner*—George Yeung
*Attorney, Agent, or Firm*—Scott B. Allison, Chrisman, Bynum & Johnson

[57] ABSTRACT

A method and apparatus are disclosed for increasing the coherency of a thin tissue section cut from a tissue sample to obtain a resulting increase in throughput of the tissue section actually transferred onto a slide for pathological evaluation. The apparatus includes an outer housing having an open end. Sealed vessel means disposed within the outer housing releasably contains ammonium hydroxide. Applicator means in fluid communication with the open end receives ammonium hydroxide released from the vessel means and is used to apply the ammonium hydroxide to an exposed surface of a tissue sample prior to cutting a tissue section from the sample. The method includes swabbing the exposed surface of the tissue sample with the applicator means for approximately ten seconds.

19 Claims, 3 Drawing Sheets

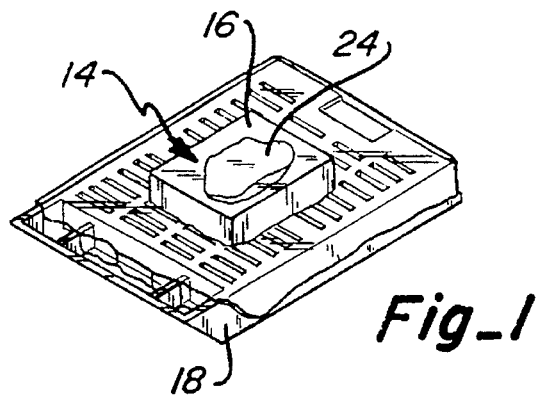
Fig_1
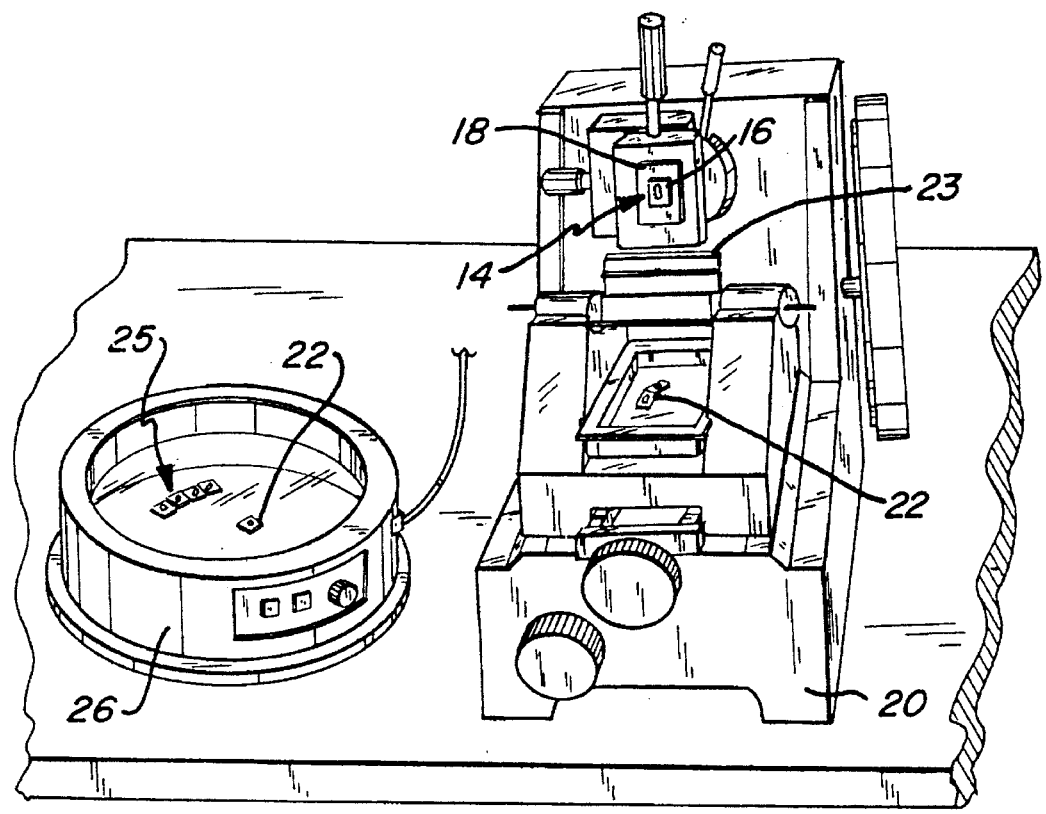
Fig_2
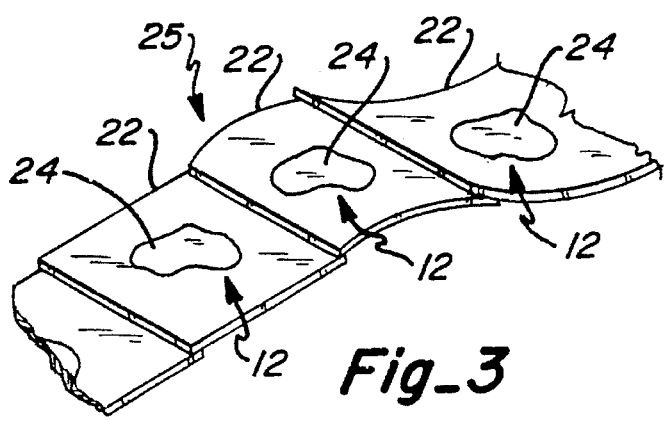
Fig_3

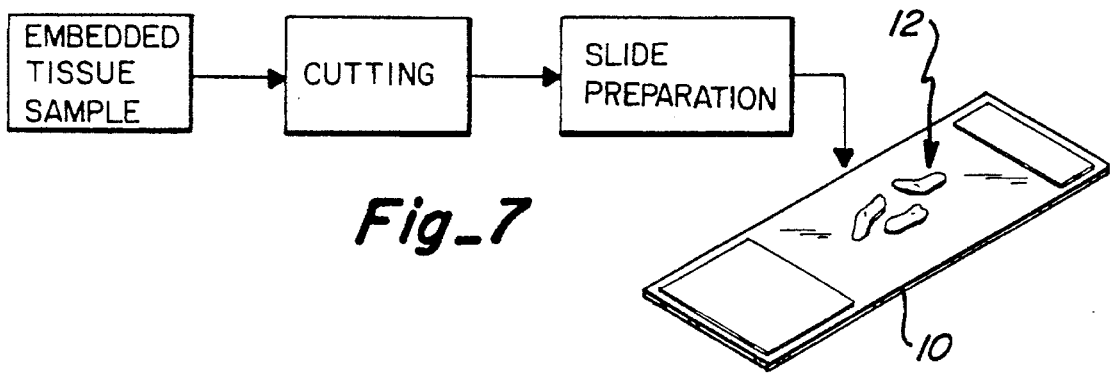
Fig_7
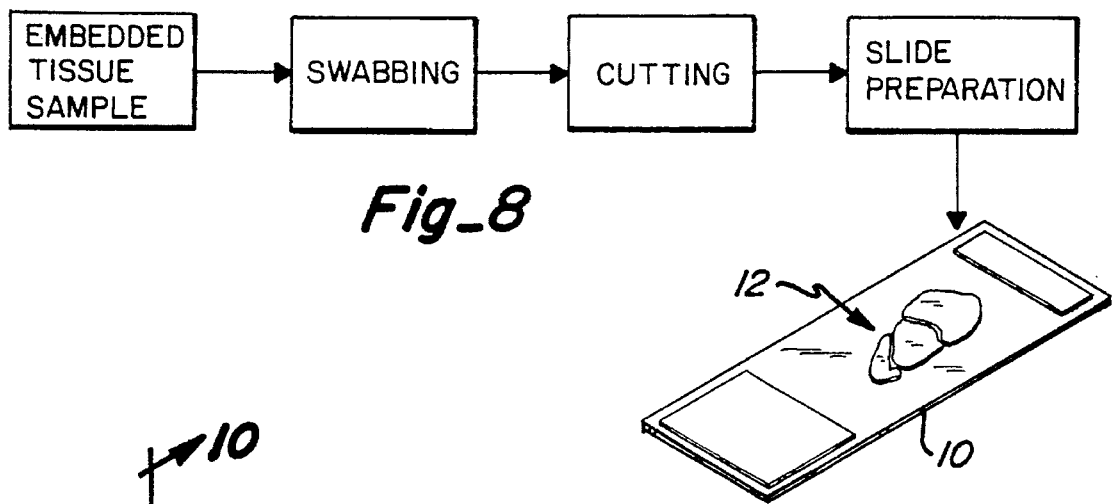
Fig_8
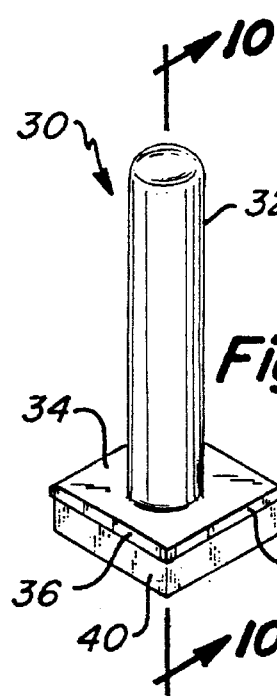
Fig_9
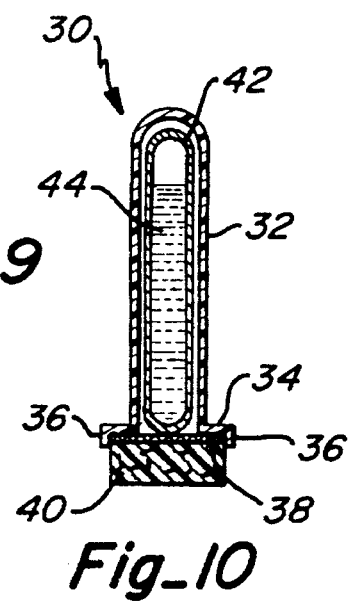
Fig_10
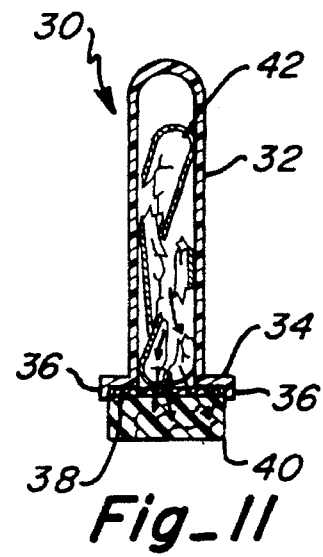
Fig_11

METHOD FOR FACILITATING TISSUE SLIDE PREPARATION

This application is a continuation of application Ser. No. 08/326,324 filed Oct. 20, 1994, now abandoned.

TECHNICAL FIELD OF THE INVENTION

This invention is generally directed to devices for facilitating tissue slide preparation and, more particularly, to a histologist's swabbing apparatus that results in a fuller and more complete tissue section deposited on a tissue slide.

BACKGROUND OF THE INVENTION

A histologist has the function of taking unprocessed tissue samples and preparing tissue slides therefrom for diagnosis by a pathologist. The importance of this work cannot be overstated since the quality of the tissue slide prepared by the histologist is critical to the ability of the pathologist to evaluate and diagnose the tissue for abnormal pathologies such as cancer or leukemia from the slide. Any small increases in the quality of the tissue slide for the pathologist's evaluation, thus have a huge impact in preventing mis-diagnosis and in minimizing the stress and fatigue of the pathologist and cost to the health care system. If the tissue slide is of unacceptable or poor quality, time and money is lost in preparing a new slide. The time lost could be critical to the patient's health by causing an undue delay in the patient's treatment.

The histologist faces difficulties in preparing a proper tissue slide because of the thinness of the tissue section to be transferred to the tissue slide. The tissue section should optimally be only one cell (e.g., approximately two to four microns) in thickness.

For example, to prepare a tissue slide for the pathologist to diagnose for leukemia, the histologist must take a sample of drawn bone marrow and cut it into thin sections. However, the bone marrow can be very brittle, like dust, and portions can flake off the sections both during and after its cutting. The resulting throughput (i.e., amount and coherency) of the tissue section actually transferred onto the slide is typically low, and may be of too marginal or poor quality for the pathologist to use. The histologist is forced to reject that section, and cut and select additional sections until a suitable section is obtained. This procedure is time consuming, inefficient, and costly.

In order to increase the quality of the tissue section transferred onto the slide, a few histologists try attempt to rub ammonium hydroxide onto the surface of the tissue sample from which the tissue section is to be cut prior to cutting. This is typically performed with an ammonium hydroxide soaked pad. However, there are several problems with this technique. Ammonium hydroxide, which is caustic, evaporates quickly and will rapidly penetrate the surrounding atmosphere. This exposes the histologist to noxious fumes which irritate the sinuses and produce eye watering and also can cause a base burn if it gets on the skin. Furthermore, because of the quick evaporation, the histologist is forced to constantly re-soak the gauze with additional ammonium hydroxide. Additionally, because ammonium hydroxide is a CAP/OSHA scheduled hazardous substance, the gauze must be soaked under a ventilation hood, typically located in a laboratory away from where the slicing takes place. Thus, this procedure is unsafe, inefficient, time consuming, and unpleasant to the histologist. As a result, fewer and fewer histologist's are using ammonium hydroxide to increase the throughput of the tissue section transferred onto the slide.

Additionally, laboratory training for histologist's, and other laboratory technicians, has increasingly shifted to training in the use of off-the-shelf products. For example, histology students in the past were taught how to make required chemical agents such as Schiff's Reagent, Hematoxylin, and Carbol Fuchsin. However, all of these are now sold in off-the-shelf product form and their method of manufacture is no longer being taught to histology students. Since no commercially available off-the-shelf, ready to use, product currently exists to train students to use ammonium hydroxide in preparing their slides, fewer and fewer histology students are even being taught of the beneficial use of ammonium hydroxide in increasing the quality of their prepared slides. Thus, the art is dying.

In view of the foregoing, a need exists for an apparatus that a histologist can conveniently use while preparing a tissue slide to increase the quality of the slide. It would be beneficial if the apparatus allowed the histologist to safely apply ammonium hydroxide to a tissue sample to increase the resulting throughput of a tissue section cut from the sample transferred onto a slide with minimal exposure to the ammonium hydroxide. It would further be beneficial if such an apparatus could help to minimize re-cut requests thereby facilitating the prompt treatment of patients. It would further be beneficial if the apparatus minimized the amount of ammonium hydroxide evaporated to the atmosphere and maximized the amount of ammonium hydroxide for applying to the embedded tissue sample. It would additionally be beneficial if the apparatus provided a ready to use product which could immediately be used as an off-the-shelf product, without preparation or assembly. Such an apparatus could be ordered by laboratories, and the like, so as to be readily and easily accessible to a large percentage of the population of histologists and histological students.

DISCLOSURE OF THE INVENTION

The present invention addresses the aforementioned needs by providing a histologist's swabbing apparatus for swabbing an exposed surface of a tissue sample to increase the coherency of a tissue section cut therefrom. In its broadest sense, the apparatus is provided with an outer housing containing ammonium hydroxide having an open end and applicator means in fluid communication with the outer housing open end for receiving ammonium hydroxide contained within the outer housing and for applying the received ammonium hydroxide onto the exposed tissue surface. The apparatus may alternatively be provided with sealed vessel means disposed within the outer housing for releasably containing a selected amount of ammonium hydroxide therein.

In the preferred embodiment of the present invention, the outer housing is comprised of flexible plastic and the sealed vessel means is comprised of a fractable plastic ampule containing ammonium hydroxide. Thus, a fracturing force can be applied through the housing to the ampule to fracture the ampule and thereby release the ammonium hydroxide contained therein. Furthermore, filter means is provided located between the outer housing open end and the applicator means. The filter means allows the ammonium hydroxide released from the ampule to pass therethrough to the applicator means while preventing broken portions of the fractured ampule from passing therethrough. The provided filter means may comprise a gauze material, and the applicator means may comprise a sponge material.

The present invention further provides a method of increasing the coherency of a tissue section cut from a tissue sample. The method includes the steps of providing a tissue sample having an exposed tissue surface and providing a histologist's swabbing apparatus. The apparatus includes an outer housing having an open end containing a selected amount of ammonium hydroxide therein. The apparatus further includes applicator means in fluid communication with the outer housing open end for receiving the ammonium hydroxide from the outer housing and for applying the received ammonium hydroxide onto the exposed tissue surface. The method further includes the steps of releasing ammonium hydroxide from the sealed vessel means to the applicator means and swabbing the exposed surface of the tissue sample with the applicator means. The method additionally includes the step of cutting a tissue section from the tissue sample.

In a preferred method of the present invention the step of swabbing is conducted for about ten seconds. Also, preferably, the method includes cooling the exposed surface after performing the step of swabbing and prior to performing the step of cutting.

BRIEF DESCRIPTION OF THE DRAWINGS

Other features of this invention will appear in the following description and appended claims, reference being made to the accompanying drawings forming a part of the specification where like referenced characters designate corresponding parts of the views.

FIG. 1 is an isometric view illustrating a tissue sample embedded in a paraffin block which has been melted onto a histologist's cassette.

FIG. 2 is a front elevation view illustrating the histologist's cassette of FIG. 1 mounted to a microtome, and a ribbon of tissue sections floating in an adjacent water bath.

FIG. 3 is an enlarged partial isometric view illustrating a ribbon tissue sections cut from the embedded tissue sample of FIG. 1.

FIG. 7 diagrammatically illustrates the slide preparation procedure not utilizing the apparatus and method of the present invention and shows an isometric view of a representative resulting tissue slide.

FIG. 8 diagrammatically illustrates the slide preparation procedure utilizing the apparatus and method of the present invention and shows an isometric view of a representative resulting tissue slide.

FIG. 9 is an isometric view illustrating the histologist's apparatus of the present invention.

FIG. 10 is vertical sectional view, taken along line 9—9 of FIG. 9, illustrating a fractable ampule containing ammonium hydroxide prior to fracture.

FIG. 11 is a vertical sectional view, taken along line 9—9 of FIG. 9, illustrating the fractable ampule after fracture with the ammonium hydroxide released onto the applicator.

BEST MODE FOR CARRYING OUT THE INVENTION

Figure 4:
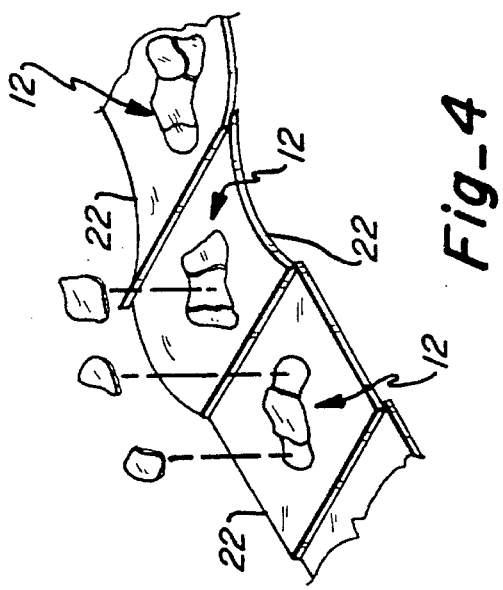
FIG. 4 is an enlarged partial isometric view illustrating bits of tissue flaking off of the tissue sections of FIG. 3.

FIGS. 1 through 3, and FIG. 7, illustrate some representative and conventional devices and procedures used by histologists in preparing a tissue slide 10, such as the glass tissue slide shown in FIG. 7. The tissue slide 10, as can be seen in FIG. 7, has deposited on it a thin tissue section 12, typically approximately one cell (e.g. between 2–4 microns) in thickness for diagnostic analysis by a pathologist. As will be further described, the tissue section 12 is cut from a tissue sample 14 which has been embedded in a paraffin block 16, as shown in FIG. 1. As can be seen in FIG. 1, the paraffin block 16 has been conventionally mounted to a cassette holder 18.

To produce a tissue slide 10, a tissue sample 14 is first conventionally removed from an organ or area to be diagnosed, such as bone marrow, liver or spleen. The tissue sample 14, typically, is then held in formaldehyde until the start of its processing. At the start of its processing, the tissue sample 14 is then penetrated at the cellular level under heat and vacuum with paraffin, in a manner known to those of ordinary skill in the art, to help maintain the cellular structure of the tissue sample 14. Thereafter, also in a manner known to those of ordinary skill in the art, the tissue sample 14 is embedded in a wax structure, such as a paraffin block 16. As shown in FIG. 1, the paraffin block 16 is mounted to a conventional histologist's cassette holder 18 by being melted thereto.

Figure 5:
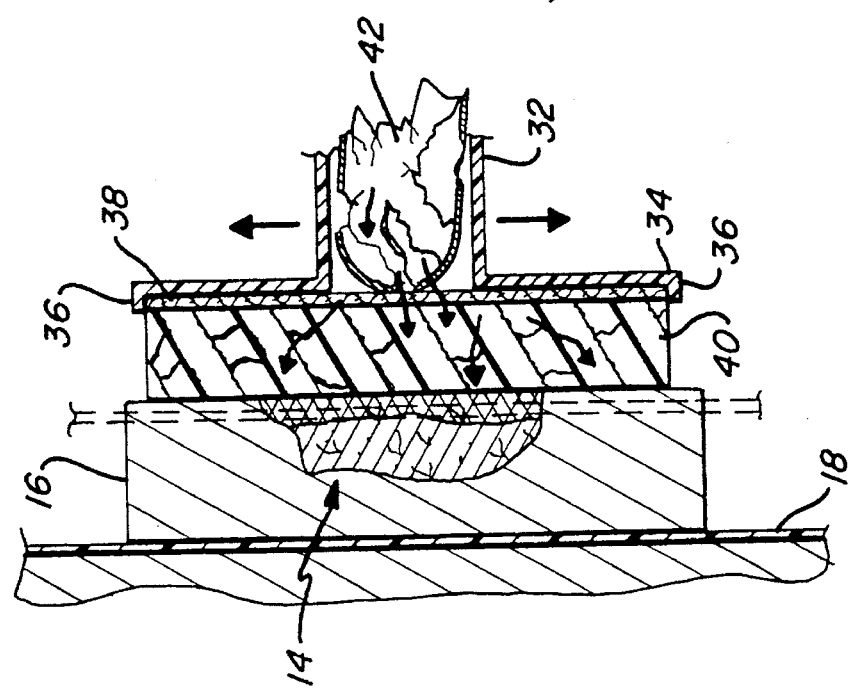
FIG. 5 is an enlarged partial side view illustrating the applicator of the present invention being used to swab an exposed surface of embedded tissue sample of FIG. 2 (microtome not shown).
Figure 6:
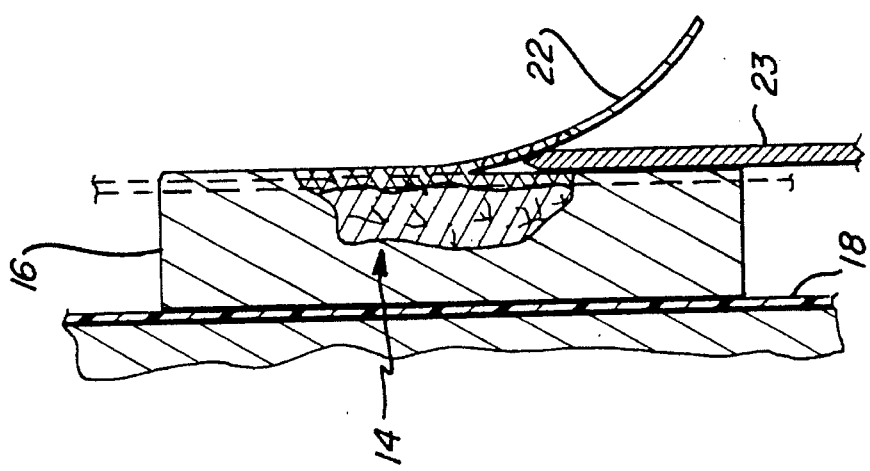
FIG. 6, in the same orientation as FIG. 5, illustrates a tissue section being cut from the embedded tissue sample having been partially penetrated with ammonium hydroxide.

As shown in FIG. 2, the cassette holder 18, with the attached embedded tissue sample 14, is then conventionally mounted to a standard laboratory microtome 20. The microtome 20 is used to cross-sectionally slice the embedded tissue sample 14 into a plurality of embedded sections 22, best seen in FIG. 3, approximately between 2 and 4 microns in thickness. More specifically, the blade 23 of microtome 20 is directed to cut the embedded tissue sample 14 in a direction generally parallel to exposed surface 24 to produce the generally flat and rectangular embedded sections 22. If necessary, prior to curing the cross-sectional sections, the paraffin block 16 is first trimmed with the blade 23 of the microtome 20 until the surface 24 of the embedded tissue sample 14 is exposed, as shown in FIGS. 5 and 6. The process of trimming also tends to generally planarize the exposed surface 24. Conventionally, as shown in FIG. 2, a plurality of embedded sections 22 may be joined in a ribbon 25, which is then floated in a warm water bath 26 to relax the paraffin and straighten the embedded sections 22. One or more of the embedded sections 22 are then selected for deposit onto a respective slide 10. After a selected embedded section 22 has been deposited on a slide 10, the slide 10 is heated at a temperature of over 60 degrees centigrade, as in a conventional laboratory oven (not shown), to melt the paraffin. The slide then is typically dipped in a paraffin dissolving agent, such as xylene, to wash the melted paraffin off of the slide. The dissolving agent, as will be understood, should not act as a dissolver to the tissue section 12 itself. Thus, only the tissue section 12 is left on the slide 10. Thereafter, the tissue section 12 is conventionally stained, nowadays typically through a conventional automatic stainer (also not shown), which dips and bathes the tissue section in independent containers containing, respectively: xylene, alcohol, water, hematoxylin and eosin. The hematoxylin, as will be appreciated, is conventionally used to stain the nucleus of the tissue section 12 and the eosin to stain the cytoplasm of the tissue section. In this manner, the tissue slide 10 is prepared for pathological examination.

A recurring problem for histologists is that, in the process of cutting the tissue sample 14 into embedded sections 22, and also during the post-slicing preparation of the embedded section 22 to a final slide 10, portions of the tissue sections 12 can flake away and separate from the remainder of the section 12. This is represented in FIG. 4. The problem is particularly persistent for hemorrhagic (i.e., bloody) tissue samples such as bone marrow samples, ectopic pregnancy samples, dilation and curettage samples, and liver and spleen samples as further examples. Additionally, flakage also frequently occurs during the staining process, previously described, as well. Thus, as diagrammatically shown in FIG. 7, simply taking an embedded tissue sample 14, cutting it, and preparing a tissue slide 10 therefrom will in many cases result in a poor quality tissue section 12 being deposited on the slide 10, as representatively illustrated on the tissue slide 10 in the figure.

A counter to this problem, as diagrammatically shown in FIG. 8, is provided by swabbing an amount of ammonium hydroxide on the surface of the embedded tissue sample 14 prior to cutting an embedded tissue section 22 therefrom. If performed properly, the additional step of swabbing increases the quality and coherency of the tissue section 12 deposited on the tissue slide 10, as representatively illustrated in FIG. 8. However, as previously described, many problems in conventional techniques have minimized this beneficial use of ammonium hydroxide. Having outlined the context of the present invention, its features and method of use will now be discussed in detail.

In accordance with this invention, a histologist's swabbing apparatus 30 is provided. The apparatus 30 is primarily designed for use by histologist's to increase the throughput (i.e., percentage and coherency) of a tissue section 12 actually transferred on to a slide 10. The apparatus 30 is further designed for hand held usage. The apparatus is meant to act as a safe container and means for delivering ammonium hydroxide for the above stated purposes.

As shown in FIGS. 9 through 11, the apparatus 30 comprises an outer housing 32, which may be preferably extruded from a flexible medical grade plastic or other suitable flexible material. Outer housing 32 has an open end (not numbered) and is preferably cylindrical in shape, though may comprise other shapes such a rectangular or a spherical shape. The purpose of the outer housing's 32 flexibility is to simply enable it to deliver ammonium hydroxide by compressive pressure, osmosis, or gravity, or, in another embodiment, to transfer a fracturing force to a provided subcontainer. Thus, ammonium hydroxide may be contained directly within the outer housing 32, or the outer housing 32 may be used to receive a subcontainer, as will be presently described.

A flange 34, which may be extruded from a rigid medical grade plastic, extends perpendicularly from the outer housing at the open end. In a preferred embodiment, the flange 34 has a lip 36 along its perimeter and is used to contain a filter, or filter means 38. The flange 34, as best shown in FIG. 9, is generally rectangular in shape.

In a preferred embodiment, the apparatus 30 is provided with a sealed inner enclosure, or vessel means, 42 which is disposed within the outer housing 32. The sealed inner enclosure 42 contains a selected amount of ammonium hydroxide 44, preferably of any suitable laboratory grade. The inner enclosure 42 is preferably formed from a suitable fractable plastic so that it is capable of releasing the ammonium hydroxide 44 when fractured. It will be understood that the manner with which the inner enclosure 42 is capable of releasing the ammonium hydroxide (such as be fracture) is not important to the practice of the present invention, and any safe manner may be applied. It will further be understood that if the inner enclosure 42 releases the ammonium hydroxide in a manner other than by fracture, the outer housing 32 need not necessarily be flexible. For ease of manufacture, the inner enclosure 42 is preferably in the form of an ampule, as shown in FIGS. 9 through 11. In the case of a fractable inner enclosure, it is desirable that the fractable inner enclosure 42 be sized and shaped to conform to the size and shape of the outer housing 32, to minimize the amount of deflection to the outer housing 32, such as by squeezing, necessary for fracture. For example, as shown in FIGS. 9 through 11, a cylindrical outer housing should preferably contain a cylindrical inner enclosure 42. Typically, the inner enclosure 42 will contain between 0.25 oz and 2 oz of ammonium hydroxide, but could contain more.

A provided applicator, or applicator means, 40 is preferably comprised of a sponge material, and is conventionally mounted adjacent to and within the flange 34. In this manner, the applicator 40 is resultingly adjacent to the open end of outer housing 32 and in fluid communication therewith to receive the ammonium hydroxide contained within the outer housing 32, whether directly or released from vessel means 42. The applicator 40 is used for applying the ammonium hydroxide 44 onto the exposed surface 24 of the embedded tissue sample 12. The applicator 40 may be conventionally attached to the filter 38, such as with a suitable glue. It will be understood that the glue should not cover the open end of the outer housing 32 to maintain fluid communication.

The provided filter, or filter means, 38 is located interposed between the outer housing 32 open end and the applicator 40. The filter 38, which may be comprised of a suitable gauze material, is used to prevent broken portions of the fractable inner enclosure 42, when fractured, from passing therethrough to the applicator 40. The filter 38 is, however, permeable to the ammonium hydroxide to allow it to pass therethrough to be absorbed by the applicator 40. The filter 40 is conventionally attached to the flange 32, as with a suitable glue. In FIGS. 9 through 11, the filter 38 is shown sized to extend to each lip 36 of flange 34. However, as will be understood, the filter 38 may be sized smaller, so long as the filter covers the open end of outer housing 32. In this event, the applicator 40 may be glued directly to the flange, rather than as shown in FIGS. 9 through 11.

The apparatus 30 is used by the histologist after the cassette holder 18 loaded with the embedded tissue sample 14 has been mounted to the microtome 20. More specifically, the apparatus 30 is used prior to cutting the embedded tissue sample 14 into the embedded sections 22, but after the paraffin block 16 has been shaved to expose the surface 24 of the embedded tissue sample 14. In use, the preferred embodiment of apparatus 30 is grasped and the flexible outer housing 32 squeezed to until the inner enclosure 42 is fractured. As shown in FIG. 11, once the inner enclosure 42 is fractured, the ammonium hydroxide 44 is released and passes through the filter 38 to wet the applicator 40. After having been wetted by the ammonium hydroxide 44, the applicator 40 is placed against the exposed surface 24 of the embedded tissue sample 14 and the exposed tissue surface is swabbed. Preferably, the swabbing is conducted several times, or approximately for 10 seconds, to allow the ammonium hydroxide to penetrate at least the first tissue layer to be sliced, as shown in FIG. 5. Additionally, the exposed tissue surface 24 and the surrounding paraffin is preferably cooled after swabbing, such as with a conventional laboratory tissue freezing aerosol, to contract the paraffin. As shown in FIG. 6, after the penetration of the ammonium hydroxide, the embedded tissue sample 14 is cut with the blade 23 of microtome 20, in the manner previously described, into embedded sections 22. It is preferable for the histologist to re-cool and re-swab the (newly) exposed surface 24 after having cut a low plurality of embedded tissue sections 22, such as between one and four sections 22. In between swabbings, the apparatus 30 can be rested sideways thus preserving the ammonium hydroxide contained inside the outer housing 12.

From the foregoing, it will be appreciated that a histologist's swabbing apparatus 30 of the present invention is provided which allows a histologist to more safely and conveniently apply ammonium hydroxide to the exposed surface 24 of an embedded tissue sample 14 to increase the throughput of the tissue sections 12 cut therefrom transferred onto a tissue slide 10. It will further be appreciated that the foregoing invention significantly reduces the treatment times for patients waiting for pathological diagnosis by minimizing the need for re-cuts. It will further be appreciated that the present invention provides an off-the-shelf product which allows histology students and histologists to be easily and readily trained to use ammonium hydroxide to increase the quality of their tissue slides, thus helping to preserve histological training in this beneficial use of ammonium hydroxide. It will be further understood that the present invention fills a need created by the shift in laboratory teaching and practice to ready made products and to less time consuming techniques. It will additionally be appreciated that the present invention diminishes the unpleasantness of the histological use of ammonium hydroxide, further inducing its beneficial use. Finally, it will be appreciated that the present invention results in faster, higher quality and less costly pathological diagnoses.

While the above invention has been shown and described in detail in this application, it should be understood that this invention is not to be limited to the exact form disclosed and changes in detail and construction of the invention may be made without departing from the spirit thereof.

We claim:

1. A method of increasing the coherency of a tissue section that is cut from a wax material embedded tissue sample and reducing the amount of fumes created during the creation of the tissue section, comprising the steps of:

penetrating the tissue sample at its cellular level with a wax material;

embedding said penetrated tissue sample in said wax material;

cutting said wax material and said penetrated tissue sample such that a generally flat surface of said penetrated tissue sample embedded in said wax material is exposed;

providing a hand-held swabbing apparatus including:
   a hollow outer housing having an open end and a closed end;
   a frangible ampoule containing ammonium hydroxide wherein said frangible ampoule is irremovably contained within said hollow outer housing; and
   an applicator in fluid communication with said open end of said hollow outer housing such that said ammonium hydroxide can flow from said frangible ampoule in said hollow outer housing through said open end of said hollow outer housing to said applicator and be received by said applicator after said frangible ampoule has been broken;

breaking said frangible ampoule contained within said hollow outer housing of said swabbing apparatus to release said ammonium hydroxide contained within said frangible ampoule;

directing said ammonium hydroxide from said broken frangible ampoule contained within said hollow outer housing to said applicator such that at least a portion of said ammonium hydroxide in said broken frangible ampoule contained within said hollow outer housing is received by said applicator;

swabbing said exposed flat surface of said penetrated tissue sample embedded in said wax material with said applicator such that at least a portion of said ammnonium hydroxide received by said applicator penetrates into said exposed flat surface of said penetrated tissue sample; and cutting said penetrated tissue sample and said wax material generally parallel to said exposed flat surface of said penetrated tissue sample to create the tissue section.

2. The method of claim 1, including the step of contracting said wax material.

3. The method of claim 1, wherein said hollow outer housing has a generally cylindrical shape and is oriented perpendicularly to said applicator such that said closed end of said hollow outer housing is positioned distally from said applicator.

4. The method of claim 2, wherein said step of contracting said wax material is performed after the step of swabbing said exposed flat surface of said penetrated tissue sample embedded in said wax material with said applicator and before said step of cutting said penetrated and embedded tissue sample and said wax material generally parallel to said flat exposed surface of the penetrated tissue sample.

5. The method of claim 1, wherein said wax material comprises paraffin.

6. The method of claim 1, including a filter interposed between said open end of said hollow outer housing and said applicator.

7. The method of claim 6, wherein said filter comprises a gauze material.

8. The method of claim 1, wherein said applicator comprises a sponge material.

9. The method of claim 1, including the step of dissolving said wax material after said tissue section is created.

10. The method of claim 1, wherein said tissue section has a thickness in a range between two (2) microns and four (4) microns.

11. A method for increasing the throughput of a tissue section that is cut from a tissue sample embedded in a wax material and allowing the preparer of the tissue section to apply liquid ammonium hydroxide to the tissue sample while limiting the amount of ammonium hydroxide fumes from the liquid ammonium hydroxide, comprising the steps of:

penetrating the tissue sample at its cellular level with a first portion of a wax material;

embedding said penetrated tissue sample within a second portion of said wax material, wherein said second portion of said wax material has a width;

trimming said penetrated tissue sample embedded in said second portion of said wax material and said second portion of said wax material such that a generally flat surface of said penetrated tissue sample embedded in said second portion of said wax material is exposed;

providing a swabbing apparatus including:

a hollow outer housing wherein said hollow outer housing has a generally cylindrical shape, an open end, and a closed end;

a frangible ampoule containing liquid ammonium hydroxide wherein said frangible ampoule has a generally cylindrical shape and is irremovably contained within said hollow outer housing; and an applicator having a top surface and a bottom surface, wherein said bottom surface of said applicator has a width, said top surface of said applicator is rigidly connected to said hollow outer housing, and said applicator is in fluid communication with said open end of said hollow outer housing such that, after said frangible ampoule is broken, said liquid ammonium hydroxide can flow from said frangible ampoule in said hollow outer housing through said open end of said hollow outer housing to said applicator, be received by said applicator, and flow within said applicator to said bottom surface of said applicator, wherein said top surface of said applicator is oriented perpendicularly to said hollow outer housing such that said closed end of said hollow outer housing is positioned distally from said top surface of said applicator, and further wherein said width of said bottom surface of said applicator is less than said width of said second portion of said wax material;

breaking said frangible ampoule contained within said hollow outer housing of said swabbing apparatus to release said liquid ammonium hydroxide contained within said frangible ampoule;

directing said liquid ammonium hydroxide from said broken frangible ampoule contained within said hollow outer housing to said applicator such that at least a portion of said liquid ammonium hydroxide in said frangible ampoule contained within said hollow outer housing is received by said applicator and flows to said bottom surface of said applicator;

swabbing said exposed flat surface of said penetrated tissue sample embedded in said second portion of said wax material with said bottom surface of said applicator such that at least a portion of said liquid ammonium hydroxide penetrates into said exposed flat surface of said penetrated tissue sample embedded in said second portion of said wax material; and cutting said penetrated tissue sample embedded in said second portion of said wax material and said second portion of said wax material generally parallel to said exposed surface of said penetrated tissue sample embedded in said second portion of said wax material to create the tissue section.

12. The method of claim 11, including the step of contracting said first and second portions of said wax material.

13. The method of claim 12, wherein said step of contracting said first and second portions of said wax material is performed after said step of swabbing said exposed flat surface of said penetrated tissue sample embedded in said second portion of said wax material.

14. The method of claim 11, wherein said wax material comprises paraffin.

15. The method of claim 11, including a filter interposed between said open end of said hollow outer housing and said top surface of said applicator.

16. The method of claim 11, wherein said sealed vessel contained within said hollow outer housing releasably contains between 0.25 and 2.0 ounces of said liquid ammonium hydroxide.

17. The method of claim 11, wherein said bottom surface of said applicator is substantially flat.

18. The method of claim 17, wherein said bottom surface of said applicator has a substantially square shape.

19. The method of claim 11, wherein during said step of swabbing said exposed flat surface of said penetrated tissue sample embedded in said second portion of said wax material with said bottom surface of said applicator, substantially all of said bottom surface of said applicator stays in physical contact with said exposed flat surface of said penetrated tissue sample embedded in said second portion of said wax material or said second portion of said wax material.

* * * * *